United States Patent [19]
Breuninger

[11] Patent Number: 5,932,748
[45] Date of Patent: Aug. 3, 1999

[54] PROCESS FOR PERMETHYLATING NON-α-TOCOPHEROLS TO PRODUCE α-TOCOPHEROL

[75] Inventor: Manfred Breuninger, Bad Säckingen, Germany

[73] Assignee: Roche Vitamins Inc., Parsippany, N.J.

[21] Appl. No.: 09/080,755

[22] Filed: May 18, 1998

[30] Foreign Application Priority Data

Jun. 6, 1997 [EP] European Pat. Off. ............. 97109174

[51] Int. Cl.⁶ .................................................. C07D 311/74
[52] U.S. Cl. ............................................................ 549/412
[58] Field of Search ............................................ 549/412

[56] References Cited

U.S. PATENT DOCUMENTS

| | | | |
|---|---|---|---|
| 2,486,539 | 11/1949 | Weisler | 549/412 |
| 2,519,863 | 8/1950 | Weisler | 549/412 |
| 3,819,657 | 6/1974 | Baldwin et al. | 549/412 |
| 4,925,960 | 5/1990 | Lechtken et al. | 549/412 |

FOREIGN PATENT DOCUMENTS

| | | |
|---|---|---|
| 176 690 | 4/1986 | European Pat. Off. . |
| 178400 | 4/1986 | European Pat. Off. . |
| 338429 | 10/1989 | European Pat. Off. . |
| 769497 | 4/1997 | European Pat. Off. . |
| 23 51 272 | 5/1974 | Germany . |

OTHER PUBLICATIONS

Catalysis Today, vol. 11, No. 2, pp. 173–291 (1991).
Appl. Catalysis A: General, vol. 119, pp. 241–252 (1994).
Appl. Catalysis A: General, vol. 145, pp. 141–153 (1996).
Appl. Catalysis A: General, vol. 145, pp. 225–230 (1996).

*Primary Examiner*—Bernard Dentz
*Attorney, Agent, or Firm*—George W. Johnston; Dennis P. Tramaloni

[57] ABSTRACT

A process for the conversion of non-α-tocopherols into (α-tocopherol by the catalytic permethylation is disclosed. The methylating agent is methanol in the near-critical or super-critical pressure and temperature region or a mixture which is equivalent to methanol and which in particular consists of hydrogen and carbon monoxide and/or carbon dioxide. The catalyst is a mixed oxide catalyst which is produced from hydrotalcites and which has at least copper and magnesium oxide as well as at least one oxide of a trivalent metal, e.g., aluminium oxide, iron(III) oxide, vanadium oxide, chromium oxide and/or gallium oxide. The product of this process has a very high content of α-tocopherol, which is the biologically most valuable tocopherol.

24 Claims, No Drawings

PROCESS FOR PERMETHYLATING NON-α-TOCOPHEROLS TO PRODUCE α-TOCOPHEROL

BACKGROUND OF THE INVENTION

The present invention is concerned with a process for the permethylation of so-called "non-a-tocopherols" to α-tocopherol using methanol or an equivalent gaseous mixture under near-critical or super-critical conditions and using a particular catalyst.

As is known, the naturally occurring non-α-tocopherols, β-, γ- and δ-tocopherol, differ from α-tocopherol (which has the highest vitamin E activity and which is accordingly the biologically most valuable tocopherol), by the absence of one or two methyl groups in the 5- and/or 7-position of the chromane part of the molecule. Accordingly, there is a need to convert such non-α-tocopherols into α-tocopherol chemically, the main problem lying in the efficient, complete mono- or, respectively, dimethylation of the benzene ring of the substituted chromanyl group.

Synthetic processes for the manufacture of nature-identical α-tocopherol have hitherto been found to be uneconomical. Natural, especially plant, sources of tocopherols usually contain predominantly non-α-tocopherols in addition to a relatively low content of α-tocopherol. For this reason, the isolation of α-tocopherol from such natural materials (raw materials) is also uneconomical. Therefore, the object of the present invention is to provide a process for the conversion of non-α-tocopherols, which may be present in appropriate raw materials or obtained from these, into α-tocopherol. The process of the present invention is in many different respects more economical than previous processes for this purpose.

Some processes for the conversion of non-α-tocopherols into α-tocopherol are already known from the state of the art. For example, European Patent Publication (EP) 176 690 (Henkel Corporation) discloses a process for the methylation of non-α-tocopherols using a methylating agent in the gas/liquid phase and in the presence of a metal oxide catalyst. This is a direct, one-stage methylation of the chromane ring, which is to be seen as a complete tocopherol methylation, i.e., a permethylation.

The catalyst used for this purpose is "functionally" defined in EP 176 690 in the sense that any catalyst which is capable of inducing an alkylating reaction can be used; typically it can be a metal oxide or a mixture of several metal oxides in which the metal atom(s) is/are selected from Groups IIA, IIB, IIIA, IVA, IB, VB, VIB, VIIB and VIII of the Periodic Table. The oxides of Be, Mg, Ca, Ti, Zr, V, Mo, Cr, Mn, Tc, Fe, Co, Ni, Zn, Cd, In, Sn, Si, Al, La, Ce, Pr and Nd are indicated to be preferred metal oxides. Such catalysts can be used as such ("neat") or on an inert carrier material and can be produced in any suitable manner, even in situ. In the case of the in situ production method, for example, a metal salt is introduced into the reactor and subsequently reacted or decomposed to the corresponding metal oxide. The methylation can be effected after removal of byproducts and any unreacted reactants.

According to an example of the "external" production of such a catalyst, dry tin hydroxide is added to a solution of ammonium vanadate in aqueous oxalic acid and treated with a solution, likewise added in activated form, of partially polymerized silicon hydroxide to give a precipitate. This is dried, calcinated and shaped by pressing. In a further example of EP 176 690, solid titanium dioxide is added to an aqueous mixture of ammonium vanadate and oxalic acid and the new mixture is heated and dried, then calcinated and shaped by pressing. In both cases there are obtained oxide mixtures which however cannot be designated crystallographically as mixed oxides; rather they are vanadium oxide on a tin oxide/silicon dioxide or, respectively, titanium dioxide carrier. In EP 176 690 there is no teaching of hydrotalcites or hydrotalcite-like metal hydroxycarbonates as possible metal-containing materials from which the metal oxide or mixed oxide catalysts could be produced, not to mention catalysts containing copper oxide (copper belongs to Group Ib of the Periodic Table).

Further, in EP 176 690 a temperature range of about 390° C. to about 470° C. is mentioned as the especially favourable temperature range and the ambient (i.e., atmospheric) pressure is mentioned as the most preferred pressure. Moreover, the use of excess methylating agent or an inert carrier gas, e.g., nitrogen, but not of an additional solvent, is foreseen.

SUMMARY OF THE INVENTION

It has now surprisingly been found that the known process of the Henkel Corporation can be improved decisively by a particular choice of catalyst and of the other reaction conditions. The object of the present invention is a process of the conversion of non-α-tocopherols into α-tocopherol by the catalyzed permethylation of at least one non-α-tocopherol using a methylating agent. The process comprises using methanol as the methylating agent where the methanol is in the near-critical or super-critical pressure and temperature range. Alternatively, a mixture equivalent to methanol consisting of hydrogen and carbon monoxide and/or carbon dioxide may be utilized in place of or in partial replacement of methanol for the methylation. As the catalyst, a mixed oxide catalyst which is produced from hydrotalcites and which contains at least copper and magnesium oxide as well as at least one oxide of a trivalent metal is used.

DETAILED DESCRIPTION OF THE INVENTION

The present invention is directed to a process for the conversion of a non-α-tocopherol into α-tocopherol. The process of the invention comprises catalytically methylating the non-α-tocopherol by contacting a reaction mixture which comprises a non-α-tocopherol source and a methylating agent (as those terms are defined, below) under near-critical or super-critical pressure and temperature conditions with a mixed oxide hydrotalcite catalyst. The catalyst comprises a divalent metal oxide phase and a trivalent metal oxide phase, wherein the divalent metal oxide phase comprises copper oxide and magnesium oxide.

As indicated above, the educt used in the process in accordance with the invention can in principle be any raw material which contains at least one non-α-tocopherol, e.g., β-, γ- or δ-tocopherol, or a tocopherol mixture which is produced or otherwise obtained from such a raw material and which likewise contains at least one non-α-tocopherol. The educt will also be referred to herein as the "non-α-tocopherol source." The tocopherol mixture is produced or otherwise obtained according to methods known in the art. Since, as is known, vegetable oils and fats, such as, for example, soya oil, rape oil, cottonseed oil, groundnut oil, wheatgerm oil, corn oil, barley oil, rye oil, thistle oil and the like, are valuable natural sources of tocopherols (inter alia α- and non-α-tocopherols), such oils or preferably their distillates, concentrates and other products, which have a higher content of tocopherols and contain fewer undesired other components, e.g., sterols, free and esterified fatty acids, waxes and glycerides, can be used as the educt in the process in accordance with the invention.

However, the presence of sterols and the other named components does not significantly impair the process in accordance with the invention. Thistle oil and soya oil in particular have been found to be valuable sources of tocopherols, inter alia α-tocopherol and the non-α-tocopherols to be converted into this in accordance with the invention. It is, of course, irrelevant whether or not α-tocopherol itself is present in the educt, since the α-tocopherol does not prevent the conversion of the non-α-tocopherols into α-tocopherol and itself remains unreacted in the product of the process.

The methanol in the near-critical or super-critical state, which is used in the process in accordance with the invention, is methanol which is heated to a temperature of at least about 240° C. and which is under a pressure of at least about 50 bar (5 MPa). At the minimum temperature of 240° C., the super-critical range starts with a pressure of about 77.5 bar (7.75 MPa). An addition of up to about 20 volume percent of water to the methanol can increase the selectivity of the methylation, but reduces its velocity.

As an alternative to the methanol in the near-critical or super-critical state, i.e. in full or partial replacement of methanol itself, sources of methanol can be used in the process in accordance with the invention. Such sources of methanol, which may also be designated as "equivalent mixtures", may be any conventional reactants which form methanol under the conditions of near critical or super critical conditions described herein for carrying out the process of the invention with methanol itself. Preferably, such a methanol source is either a mixture of hydrogen and carbon monoxide which is equivalent to methanol, or the equivalent mixture of hydrogen and carbon dioxide, or the equivalent mixture of hydrogen and both carbon monoxide and carbon dioxide.

The first-named mixture is a mixture which is basically suitable for the synthesis of methanol. Accordingly this mixture contains hydrogen and carbon monoxide in the molar ratio in the range from about 2:1 to about 20:1. The hydrogen/carbon monoxide mixture is used under the same pressure and temperature conditions as methanol.

The second-named "equivalent mixture" is also one which is basically suitable for the synthesis of methanol. In this case the molar ratio hydrogen:carbon dioxide is in the range from about 3:1 to about 20:1 and the mixture is also used under the same pressure and temperature conditions as methanol.

With respect to the synthesis of methanol from such "equivalent mixtures", reference is made, for example, to *Catalysis Today*, Vol. 11, No. 2, pages 173–291, especially pages 230–235 (1991), in which also the third-named "equivalent mixture" is also described.

An especially suitable equivalent mixture is the third-named "equivalent mixture", i.e. one which contains hydrogen and both carbon monoxide and carbon dioxide and which accordingly can be regarded as a combination of the first- and second-named "equivalent mixtures". The above-indicated molar ratio ranges of hydrogen:carbon monoxide and hydrogen:carbon dioxide apply within such three-component mixtures in the sense that there should be at least about 2 moles of hydrogen for every mole of carbon monoxide present and at least a further about 3 moles of hydrogen for every mole of carbon dioxide present. The principle applies for the upper limit of the molar ratio of hydrogen to carbon monoxide and of hydrogen to carbon dioxide, i.e. about 20:1 in each case. On pages 230–235 of the aforementioned *Catalysis Today* reference mixtures of all three gases are given with molar ratios $H_2:CO:CO_2$ about 65:32:3 and about 86:8:6, the first of which clearly representing the very lower limit in respect of the molar amount of hydrogen to the molar amounts of the other two gases in the mixture. In general, the greater the amount of hydrogen with respect to the amount of carbon monoxide and/or carbon dioxide, the more hydrogen remains unreacted in the reaction(s) forming methanol; excessive presence of hydrogen is clearly uneconomical.

For the purposes of the present invention, methanol itself, any source of methanol as described hereinabove, and any mixture of methanol and a source of methanol shall in each case be referred to as a "methylating agent."

The so-called hydrotalcites, from which the mixed oxide catalyst used in accordance with the invention is produced, are a known class of isomorphic minerals which occur in nature and which in each case are mixed hydroxycarbonates of different metals, e.g., magnesium and aluminium or magnesium and iron. "Hydrotalcite" itself has the chemical formula $Mg_6Al_2(OH)_{16}CO_3 \cdot 4H_2O$ and other minerals having a similar structure are present in nature or have been synthesized, such as sjögrenite and pyroaurite. The latter minerals are conventional hydrotalcite-like compounds. In the scope of the present invention, hydrotalcite and hydrotalcite-like compounds which have the recognized general formula $[M(II)_{1-x}M(III)_x(OH)_2]^{x+}(A^{n-}x/n) \cdot mH_2O$, wherein M(II) and M(III) are divalent and trivalent metal ions, respectively, $A^{n-}$ is an exchangeable anion and x is 0.1–0.33, are all encompassed within the term "hydrotalcites". For relevant literature concerning hydrotalcites and their production, primarily by coprecipitation, and their use as catalysts, partly as such or after calcination to mixed metal oxides, see *Catalysis Today*, Vol. 11, No. 2, 173–291 (1991) and the literature references cited therein, *Appl. Catalysis A: Geiteral*, 119, 241–252 (1994), and ibid., 145, 141–153 and 225–230 (1996).

The amount of mixed oxide catalyst used in the process of the invention is not critical, so long as measurable conversion of non-α-tocopherol to α-tocopherol occurs under the stated near-critical or super-critical conditions.

The mixed oxide catalyst produced from hydrotalcites and used in accordance with the invention contains at least copper oxide and magnesium oxide (both copper and magnesium are divalent metals) as well as at least one oxide of a trivalent metal [denoted hereinafter as "metal (III) oxide"]. The divalent metal oxides are collectively called the "divalent metal oxide phase" of the catalyst, and the trivalent metal oxides are collectively called the "trivalent metal oxide phase" of the catalyst. The term "phase" as used herein does not refer to different crystallographic phases, but merely provides a means of refering collectively to all the divalent metal oxides as a group and to all the trivalent metal oxides as a group. The metal(III) oxides are preferably oxides of aluminium and iron(III). However, oxides of other divalent and/or trivalent metals can also be present. Examples of other divalent (II) and trivalent (III) metals are beryllium(II), calcium(II), vanadium(III), chromium(III), manganese(II), iron(II), cobalt(II), nickel(II), zinc(II), gallium(III) and cadmium(II). In the most preferred embodiment of the catalyst in accordance with the present invention, the divalent metal oxide phase of the catalyst consists essentially of copper oxide and magnesium oxide, and the trivalent metal oxide phase of the catalyst consists essentially of aluminium oxide and iron(III) oxide.

In the mixed oxide catalyst which is produced from hydrotalcites and which is used in accordance with the invention, the atomic ratio of the total metals in the divalent metal oxide phase to the total metals in the trivalent metal oxide phase, is in the range from about 2:1 to about 10:1, preferably about 3:1 to about 4:1. With respect to the atomic ratio between the divalent metals present in the divalent metal oxide phase (inter alia essentially copper and magnesium), then the atomic ratio of copper to non-copper divalent metals present, is in the range from about 5:95 to about 60:40, preferably about 25:75 to about 50:50. In the preferred catalyst which contains aluminium and other trivalent metals, the atomic ratio between the aluminium and the non-aluminium trivalent metals [Al:other metals (III)] preferably amounts to about 2:1 to about 1:2, especially about 2:1.

In addition to the essentially present copper oxide, magnesium oxide and metal (III) oxide(s), there can be present in the mixed oxide catalyst used in accordance with the invention, inter alia, oxides of lithium, sodium and/or potassium as contaminants in an amount which is up to about 2% of the total weight of the mixed oxide catalyst. These alkali metals are normally present because alkali metal bases are required for the production or working up of the mixed oxide catalyst and are not washed out completely. As used herein, the delineation of a specific composition for a catalyst does not exclude the possible presence of the above-described contaminants.

In principle, the process in accordance with the invention is carried out by conducting the non-o:-tocopherol source, which may be dissolved in an inert solvent, together with the methylating agent under near-critical or super-critical pressure and temperature conditions through a reactor loaded with the mixed oxide catalyst, e.g., a heated tube loaded with the catalyst. The crude product which flows from the reactor then only needs to be separated, e.g., by distillation, from the gases which result in the methylation, primarily hydrogen and carbon monoxide, as well as from excess methanol and any residual inert solvents used. After the methylation and any separation of gases, excess methanol, and solvents, etc., the product enriched in α-tocopherol can, if desired, be subjected repeatedly to the process in accordance with the invention in order each time to obtain a product which is more strongly enriched in α-tocopherol, if the intended purpose of use makes this necessary, i.e., in order to achieve the required degree of conversion to α-tocopherol. The nature of a catalytic process is such that the desired degree of conversion can also be achieved by lengthening the contact time of the non-α-tocopherol source on the catalyst, by increasing the amount of catalyst in the reactor or lowering the flow rate of the non-α-tocopherol source used in the reactor. No significant decomposition of the tocopherols normally occurs during the reaction.

As the aforementioned inert solvent there is used a non-polar organic solvent, preferably an alkane of medium molecular weight, primarily a $C_{5-10}$-alkane, e.g., pentane, hexane or heptane, or mixtures thereof, e.g., a petroleum ether having a boiling range between about 40° C. and about 120° C.; a $C_{5-10}$-cyclic alkane, e.g., cyclohexane, or an aromatic hydrocarbon, e.g., toluene.

When the non-α-tocopherol source is dissolved in an inert solvent—and is thus diluted—the concentration of the non-α-tocopherol source in the solvent is in the range from about 10 g/l to about 500 g/l, preferably about 100 g/l to about 500 g/l.

The amount of methanol used as the methylating agent relative to the non-α-tocopherol(s) generally corresponds to at least one equivalent of methanol per each (estimated) methylatable position in the non-α-tocopherols present in the non-α-tocopherol source. As a matter of course, an excess of methanol should be used, such as about 10 to about 1000 equivalents, preferably about 25 to about 250 equivalents.

If an equivalent mixture of hydrogen and carbon monoxide and/or carbon dioxide is used as a methanol source in place of methanol, then the amount of carbon monoxide and/or carbon dioxide likewise corresponds to at least one equivalent of methanol per each of the (estimated) methylatable positions in the non-α-tocopherol. Also in this case the amount is conveniently about 10 to about 1000 equivalents, preferably about 25 to about 250 equivalents.

Analogous considerations apply to the amount of any mixture of methanol and a source of methanol which may be used as the methylating agent.

The rate at which the optionally diluted non-α-tocopherol source is passed over the mixed oxide catalyst and also the corresponding flow rate of the methylating agent can be adjusted and correlated with respect to each other, to the amount of catalyst, to the catalyst activity, to the reaction temperature and to the reaction pressure such that the methylation proceeds as efficiently as possible having regard to conversion and reaction duration. In this case, the optimal contact times lie in the range of about 1 to about 100 minutes.

The permethylation is carried out at pressures between about 50 bar and about 120 bar (about 5 to about 12 MPa), preferably at pressures between about 70 bar and about 90 bar (about 7 to about 9 MPa), particularly at about 80–85 bar (8–8.5 MPa) (at pressures below about 77.5 bar, i.e., in the "near-critical range", a more rapid reaction takes place, but dark impurities contained in the crude product are not separated from the reactor and can adversely influence the activity of the catalyst). Moreover, an especially high reaction velocity is achieved, for example, at about 50 bar (5 MPa), but to the detriment of catalyst stability. Pressures of more than about 120 bar (12 MPa) reduce the reaction velocity and necessitate the use of expensive equipment without bringing any compensating advantages.

The reaction is carried out at a temperature in the range of about 240° C. to about 350° C., preferably in the range of about 280° C. to about 320° C.

An advantage of the process in accordance with the invention is that no recognizable racemization of the optically active centres of the non-α-tocopherols to be permethylated takes place. When a tocopherol mixture from natural sources is the educt used as the tocopherol source, there is typically obtained as the product RRR-α-tocopherol having an optical purity of at least 99.5%. Also, no other decomposition of the educt or of the product which is worthy of note takes place during the permethylation.

A further advantage resides in the fact that the catalyst can be used many times, so that, for example, in the case of an undesirably low methylation, the product obtained can again be reacted using the catalyst without the activity of the repeatedly used catalyst being noticeably reduced. In this connection, in general a large amount of non-α-tocopherol (s) can be methylated on one catalyst without a noticeable deactivation of the catalyst taking place.

The simplicity of the process and of the working up as well as the high selectivity which can be achieved make the process in accordance with the invention especially suitable for the large scale manufacture of (α-tocopherol.

The present invention is illustrated by the following Examples:

EXAMPLE 1

Production of a typical catalyst used in accordance with the invention, and a typical reactor (laboratory scale)

Production 8 g (20 mmol) of aluminium nitrate, 4 g (10 mmol) of iron(III) nitrate, 14 g (60 mmol) of copper(II) nitrate and 15 g (60 mmol) of magnesium nitrate (all as hydrates, i.e. as the nitrate ·9H$_2$O, ·9H$_2$O, ·3H$_2$O and respectively, ·6H$_2$O) were dissolved in 240 ml of water. The resulting solution was stirred at 90° C. during 30 minutes into a solution of 30 g (360 mmol) of sodium bicarbonate in 240 ml of water. The mixture was stirred at 90° C. for a further 2 hours. The precipitate was filtered off and washed with water until the filtrate reacted neutral. This pulp-like precipitate was either dried directly at about 120° C. or previously formed using a hand syringe into "rope-like extrudates" having a diameter of about 1.5 mm. The dried catalyst precursor (as fragments or as "rope-like extrudates") was calcinated at 250–400° C. for about 4 hours with access to air. The fragments were ground in a mortar, while the "rope-like extrudates" were broken into pieces 2–5 mm in length. The thus-produced catalyst was filled into a reactor.

Reactor

The reactor consisted of an upright high-pressure tube which was heated via a thermostatically controlled oil heating jacket. The tube had an internal diameter of 7.8 mm, a heated length of 25 cm and an overall length of about 40 cm.

A tube closed on one side and having an external diameter of 3.2 mm was present in the reactor and over the entire length and served as a housing for a thermoelement with which the temperature in the longitudinal axis of the entire reactor could be measured.

The outlet, which was covered with a filter, was situated at the lower end of the reactor. The space between filter and the beginning of the heating zone was filled with sea sand. The catalyst was placed above this, giving different catalyst bed depths according to amount and bulk density. The space above the catalyst bed was empty.

The pressure monitor, a breakable disk and the inlet for the educt were situated at the upper end of the reactor. Two high pressure pumps supplied methanol and the additional solvent (e.g., toluene, hexane or additional methanol) to the reactor. One liquid stream—usually the larger—was preheated. The non-α-tocopherol was admixed as the educt with the non-heated stream, so that the adjustment could be made from pure solvent to educt solution.

The outlet was connected to a pressure-tight valve with which the pressure in the reactor could be adjusted. From there the product solution was conducted into a receiver.

EXAMPLE 2

A catalyst powder, calcinated at 350° C. and still containing about 0.5% sodium, was prepared from a solution of the nitrates of iron(III) (10 mmol), aluminium (20 mmol), magnesium (60 mmol) and copper(II) (60 mmol). 1.8 g (3.5 ml) of this catalyst were filled into the reactor. At 320° C. there were pumped into the reactor 1.25 ml/min. of pre-heated hexane with the first pump and 0.625 ml/min. of methanol with the second. The pressure was adjusted to 100 bar (10 MPa).

Then, 3 ml of a methanolic solution containing 1 g of RRR-γ-tocopherol in place of methanol were pumped in with the second pump. Subsequently, further methanol was pumped in during 40 minutes in order to flush the product from the reactor. The total product solution was collected in the receiver, evaporated and analyzed by gas chromatography (GC). The evaporation residue contained 86.0 GC area-% α- and 3.9 GC area-% γ-tocopherol. Further investigation indicated that the optical activity of the educt had been retained and that at the most 1 weight-% of 2S-isomers was obtained.

In a further experiment on the same catalyst packing using the same conditions (temperature, pressure and flow velocities) as above, 3 ml of a methanolic solution containing 1 g of RRR-δ-tocopherol were pumped in. The evaporated product solution contained 53.85 GC area-% α- and 21.94 GC area-% β/γ-tocopherol.

EXAMPLE 3

"Rope-like extrudates", calcinated at 350° C., were produced as the catalyst from a solution of the nitrates of iron(III) (10 mmol), aluminium (20 mmol), magnesium (60 mmol) and copper(II) (60 mmol).

3.0 g (6 ml) of this catalyst were filled into the reactor. At 300° C. there were pumped into the reactor 2.25 ml/min. of hexane with the first pump and 0.75 ml/min. of pre-heated methanol/water (9/1 v/v) with the second. The pressure was adjusted to 90 bar (9 MPa). Then, 9 ml of a solution containing 1 g of RRR-5-tocopherol in hexane were pumped in in place of hexane with the first pump. Subsequently, hexane was again pumped in during about 60 minutes in order to flush the product from the reactor. The entire product solution was collected in the receiver, evaporated and analyzed by GC.

The evaporation residue was again made up to 9 ml with hexane and, as above, pumped through the reactor and analyzed.

In this manner the tocopherol was pumped through the reactor a total of eleven times. The analytical results of the individual methylation steps are compiled in Table 1 hereinafter.

TABLE 1

| Methylation Passage | α-Tocopherol GC area % | γ-Tocopherol GC area % | β-Tocopherol GC area % | δ-Tocopherol GC area % |
|---|---|---|---|---|
| 1 | 23.7% | 4.6% | 46.5% | 19.6% |
| 2 | 43.3% | 2.3% | 44.8% | 4.4% |
| 3 | 56.9% | 1.3% | 36.6% | 1.2% |
| 4 | 65.0% | 0.8% | 29.1% | 0.4% |
| 5 | 71.4% | 0.6% | 22.0% | * |
| 6 | 73.8% | 0.7% | 19.1% | * |
| 7 | 72.5% | 0.9% | 19.9% | * |
| 8 | 79.5% | 0.9% | 12.7% | * |
| 9 | 82.4% | 0.8% | 9.8% | * |
| 10 | 85.2% | 0.8% | 7.3% | * |
| 11 | 85.9% | 0.9% | 6.1% | * |

*: no longer detectable

EXAMPLE 4

"Rope-like extrudates", calcinated at 350° C., were produced as the catalyst from a solution of the nitrates of iron(III) (10 mmol), aluminium (20 mmol), magnesium (90 mmol) and copper(II) (30 mmol).

3.0 g (7 ml) of this catalyst were filled into the reactor. At 300° C. there were pumped into the reactor 3 ml/min. of hexane with the first pump and 0.75 ml/min. of pre-heated methanol/water (8/2 v/v) with the second. The pressure was adjusted to 90 bar (9 MPa).

Then, 9 ml of a solution containing 1 g of RRR-δ-tocopherol in hexane were pumped in in place of hexane with the first pump. Subsequently, further hexane was pumped in during 60 minutes in order to flush the product from the reactor. The entire product solution was collected in the receiver, evaporated and analyzed by GC.

The evaporation residue was again made up to 9 ml with hexane and, as above, pumped through the reactor and analyzed.

In this manner the tocopherol was pumped through the reactor a total of six times. The analytical results of the individual methylation steps are compiled in Table 2 hereinafter:

TABLE 2

| Methylation Passage | α-Tocopherol GC area % | γ-Tocopherol GC area % | β-Tocopherol GC area % | δ-Tocopherol GC area % |
|---|---|---|---|---|
| 1 | 27.0% | 4.1% | 39.2% | 26.7% |
| 2 | 57.4% | 1.5% | 33.5% | 3.3% |
| 3 | 71.7% | 1.2% | 21.1% | 0.5% |
| 4 | 77.3% | 1.3% | 15.2% | * |
| 5 | 80.9% | 1.5% | 11.6% | * |
| 6 | 83.7% | 1.7% | 7.9% | * |

*: no longer detectable

EXAMPLE 5

A catalyst powder, calcinated at 400° C., was produced from a solution of the nitrates of iron(III) (10 mmol), aluminium (20 mmol), magnesium (60 mmol) and copper (II) (60 mmol).

3.95 g (9 ml) of this catalyst were filled into the reactor. At 320° C. there were pumped into the reactor 9 ml/min. of pre-heated hexane with the first pump and 2.8 ml/min. of methanol with the second. The pressure was adjusted to 90 bar (9 MPa).

Then 10 ml of a methanolic solution containing 2.5 g of a non-α-tocopherol concentrate (educt) of which only about a half consisted of tocopherols, was pumped in instead of methanol with the second pump. Subsequently, further methanol was pumped in during about 60 minutes with the second pump in order to flush the product from the reactor. The collected product solution was evaporated and analyzed by GC (product 1).

In a second experiment (as above) 10 ml of a methanolic solution containing 1 g of the non-α-tocopherol concentrate (educt) described above were pumped in instead of methanol with the second pump. Subsequently, further methanol was pumped in during about 60 minutes with the second pump in order to flush the product from the reactor. The collected product solution was evaporated and analyzed by GC (product 2). The results are compiled in Table 3 hereinafter:

TABLE 3

| | α-Tocopherol | γ-Tocopherol | δ-Tocopherol | β-Tocopherol | Sterols | Remainder |
|---|---|---|---|---|---|---|
| Educt (weight %) | 3% | 27% | 13% | * | 5.6% | 50% |
| Product 1 (GC area %) | 25.8% | 17.5% | 4.6% | 7.3% | ** | ** |
| Product 2 (GC-area %) | 39.4% | 8.7% | 1.2% | 6.3% | ** | ** |

*: non detectable
**: not measured

In another experiment on this catalyst, 5 ml/min. of pre-heated hexane at 320° C. were pumped into the reactor with the first pump and 2 ml/min. of methanol with the second. The pressure was adjusted to 90 bar (9 MPa).

Then, 100 ml of a methanolic solution containing 1 g of δ-tocopherol were pumped in instead of methanol with the second pump. The product solution was collected separately every 6.5 minutes (corresponding to 12.5 ml of educt solution), evaporated and analyzed by GC. The results are compiled in Table 4 hereinafter:

TABLE 4

| Sample (GC area %) | α-Tocopherol | γ-Tocopherol | δ-Tocopherol | β-Tocopherol |
|---|---|---|---|---|
| 1 | 94.8% | 3.4% | 0% | 0.5% |
| 2 | 92.8% | 3.8% | 0% | 0.4% |
| 3 | 91.7% | 3.7% | 0% | 0.6% |
| 4 | 91.8% | 3.6% | 0% | 0.8% |
| 5 | 91.1% | 3.4% | 0% | 0.9% |
| 6 | 91.5% | 3.4% | 0% | 1.0% |
| 7 | 90.7% | 3.5% | 0% | 1.1% |

EXAMPLE 6

"Rope-like extrudates", calcinated at 350° C., were produced as the catalyst from a solution of the nitrates of iron(III) (10 mmol), aluminium (20 mmol), magnesium (60 mmol) and copper(II) (60 mmol).

3.0 g (7 ml) of this catalyst were filled into the reactor. At 300° C. there were pumped into the reactor 1 ml/min. of hexane with the first pump and 3 ml/min. of pre-heated methanol/water (9/1 v/v) with the second. The pressure was adjusted to 85 bar (8.5 MPa).

Then, 3 ml of a solution containing 0.5 g of RRR-δ-tocopherol (educt) in hexane were pumped in instead of hexane with the first pump. Subsequently, further hexane was pumped in during about 60 minutes in order to flush the product from the reactor. The entire product solution was collected in the receiver, evaporated and analyzed by GC (areα-% method).

The evaporation residue was again made up to 3 ml with hexane and, as above, pumped through the reactor and analyzed.

In this manner the tocopherol was pumped through the reactor a total of eleven times. After the last passage 0.4 g of product was still present, since eleven analytical samples each of 5–10 mg had to be removed from the reaction mixture. The analytical results of the individual methylation steps are compiled in Table 5 hereinafter:

TABLE 5

| Methylation passage | α-Tocopherol | γ-Tocopherol | β-Tocopherol | δ-Tocopherol |
|---|---|---|---|---|
| Educt | 0.8% | 4.5% | 0.1% | 94.0% |
| 1 | 30.7% | 3.8% | 48.2% | 11.1% |
| 2 | 57.3% | 1.3% | 34.2% | 1.2% |
| 3 | 72.8% | 0.7% | 20.3% | 0.3% |
| 4 | 81.7% | 0.6% | 11.7% | * |
| 5 | 86.4% | 0.7% | 6.9% | * |
| 6 | 89.3% | 0.6% | 3.9% | * |
| 7 | 90.8% | 0.6% | 2.2% | * |
| 8 | 91.2% | 0.7% | 1.4% | * |
| 9 | 91.6% | 0.7% | 0.8% | * |
| 10 | 91.3% | 0.8% | 0.5% | * |
| 11 | 91.8% | 0.8% | 0.3% | * |

*: no longer detectable

In a further experiment on this catalyst, 2.5 ml/min. of pre-heated methanol/toluene mixture (4/1 v/v) at 320° C. were pumped into the reactor with the first pump and 0.5 ml/min. of toluene with the second. The pressure was adjusted to 85 bar (8.5 MPa).

Then, 210 ml of a solution containing 7.089 g of a non-α-tocopherol concentrate in toluene were pumped in instead of toluene with the second pump. After this educt solution had been pumped in it was again replaced by toluene for about 1 hour in order to flush the product completely from the reactor. The collected product solution was evaporated.

Educt and product were accurately weighed and analyzed. The following compilation (Table 6) confirms that practically all tocopherol had been converted into RRR-α-tocopherol without the appearance of any significant decomposition.

TABLE 6

Batch and yield calculation of the quantitative experiment

| Educt | α-Tocopherl | γ-Tocopherol | β-Tocopherol | δ-Tocopherol | Remainder |
|---|---|---|---|---|---|
| Molecular weight | 430.720 | 416.693 | 416.693 | 402.666 | |
| Composition (weight %) | 3.67% | 48.51% | 1.28% | 31.30% | 15.2% |
| Batch weight (total = 7.089 g) | 0.260 g (0.603 mmol) | 3.439 g (8.252 mmol) | 0.091 g (0.218 mmol) | 2.218 g (5.509 mmol) | 1.08 g |
| Theoretic yield of α-tocopherol after methylation | 0.260 g | 8.554 g | 0.094 g | 2.373 g | |
| Total α-tocopherol according to theory: | 6.281 g | | | | |
| Product Yield calculation | | | | | |
| Found yield = 7.136 g | | | | | |
| Tocopherol content (weight %) | 83.66% | 0.81% | 1.08% | | |
| Tocopherol weight | 5.970 g | | | | |
| Chemical yield (% of theory) | 95.05% | 0.95% | 1.23% | | |
| Analysis of the methyl ether for optical activity | RRR-a 93.41% | 2S-α 0.44% | RRR-β 1.24% | | |

A further packing of the above catalyst of 3 g (6 ml) was filled into the reactor. At 270° C. 1 ml/min. of toluene was pumped into the reactor with the first pump and 2 ml/min. of pre-heated methanol with the second. The pressure was adjusted to 85 bar (8.5 MPa).

Then 5 solutions, each of 30 ml and each containing 0.5 to 8 g (see Table) of non-α-tocopherol concentrate in toluene, were pumped in successively in place of toluene with the first pump. Further toluene was pumped in between the tocopherol solutions during about 30 minutes in order to flush the product from the reactor. After the individual tocopherol solutions had been pumped in a product sample was withdrawn and analyzed by GC (areα-% method). The results listed in Table 7 hereinafter show a clear conversion into α-tocopherol, which depends on the loading of the reactor and thus on the residence time.

TABLE 7

| Sample | Educt amount (g)/30 ml | α-Tocopherol | γ-Tocopherol | β-Tocopherol | δ-Tocopherol |
|---|---|---|---|---|---|
| Educt | | 4.17% | 56.03% | 1.31% | 36.17% |
| 1 | 8.01 | 6.68% | 51.47% | 2.59% | 33.19% |
| 2 | 4.02 | 8.29% | 50.71% | 3.72% | 31.99% |
| 3 | 2.02 | 11.38% | 48.47% | 6.04% | 29.08% |
| 4 | 1.09 | 18.49% | 42.41% | 10.17% | 23.15% |
| 5 | 0.51 | 28.46% | 34.89% | 13.89% | 17.05% |

In a further series of experiments, 1 ml/min. of toluene at 300° C. was pumped into the reactor with the first pump and 2 ml/min. of pre-heated methanol with the second. The pressure was again adjusted to 85 bar (8.5 MPa).

Then, a further 5 solutions, each of 30 ml and each containing 0.5 to 8 g (see Table) of non-α-tocopherol concentrate in toluene, were pumped in instead of toluene with the first pump. Further toluene was pumped in between the tocopherol solutions during about 30 minutes in order to flush the product from the reactor. After the individual tocopherol solutions had been pumped in a product sample was withdrawn and analyzed by GC (area % method). The results listed in Table 8 hereinafter show once again a clear conversion into α-tocopherol which depends on the loading of the reactor and thus on the residence time. Also, this series shows in comparison to the above series that at higher temperature a greater conversion takes place with otherwise equal conditions.

TABLE 8

| Sample | Educt amount (g)/30 ml | α-Toco-pherol | γ-Toco-pherol | β-Toco-pherol | δ-Toco-pherol |
|---|---|---|---|---|---|
| Educt | | 4.17% | 56.03% | 1.31% | 36.17% |
| 1 | 8.02 | 16.51% | 44.22% | 8.58% | 25.03% |
| 2 | 4.00 | 27.99% | 35.25% | 14.20% | 16.60% |
| 3 | 2.00 | 49.66% | 19.82% | 18.39% | 6.24% |
| 4 | 1.02 | 58.07% | 6.62% | 11.65% | 1.46% |
| 5 | 0.52 | 80.71% | 4.60% | 6.71% | 0.46% |

I claim:

1. A process for the conversion of a non-α-tocopherol into α-tocopherol which process comprises catalytically methylating said non-α-tocopherol by contacting a reaction mixture which comprises a non-α-tocopherol source and a methylating agent under near-critical or super-critical pressure and temperature conditions with a mixed oxide hydrotalcite catalyst which catalyst comprises a divalent metal oxide phase and a trivalent metal oxide phase, wherein said divalent metal oxide phase comprises copper oxide and magnesium oxide, whereby said non-α-tocopherol is converted to said α-tocopherol.

2. The process of claim 1 wherein said methylating agent is present in an amount which corresponds to about 10 equivalents to about 1000 equivalents of methanol per each methylatable position in the non-α-tocopherols present in the non-α-tocopherol source, the pressure at which the methylation is carried out is in a range from about 50 bar and to about 120 bar, and the temperature at which the methylation is carried out is in a range from about 240° C. to about 350° C.

3. The process of claim 2 wherein the methylating agent is methanol.

4. The process of claim 3 wherein said methanol source is present in an amount from about 25 equivalents to about 250 equivalents per each methylatable position in the non-α-tocopherols present in the non-α-tocopherol source, the pressure at which the methylation is carried out is in a range from about 50 bar and to about 120 bar, and the temperature at which the methylation is carried out is in a range from about 240° C. to about 350° C.

5. The process of claim 4 wherein the trivalent metal oxide phase comprises aluminium oxide, iron(III) oxide, vanadium oxide, chromium oxide or gallium oxide.

6. The process of claim 5 wherein the trivalent metal oxide phase comprises aluminium oxide and a trivalent metal oxide selected from the group consisting of iron(III) oxide, vanadium oxide, chromium oxide or gallium oxide.

7. The process of claim 6 wherein the trivalent metal oxide phase comprises aluminium oxide and iron(III) oxide.

8. The process of claim 7 wherein the atomic ratio of the total divalent metals to the total trivalent metals is in the range from about 2:1 to about 10:1, and the atomic ratio of copper to non-copper divalent metals is in a range from about 5:95 to about 60:40.

9. The process of claim 8 wherein the atomic ratio of the total divalent metals to the total trivalent metals is in the range from about 3:1 to about 4:1.

10. The process of claim 9 wherein the divalent metal oxide phase consists essentially of copper oxide and magnesium oxide, and the trivalent metal oxide phase consists essentially of aluminium oxide and iron(III) oxide.

11. The process of claim 10 wherein the atomic ratio of copper to magnesium is in a range from about 25:75 to about 50:50, and the atomic ratio of aluminium to iron(III) is in a range from about 2:1 to about 1:2.

12. The process of claim 11 wherein the pressure is in a range from about 70 bar to about 90 bar, and the temperature is in a range from about 280° C. to about 320° C.

13. The process of claim 12 wherein the pressure is in a range from about 80 bar to about 85 bar.

14. The process of claim 4 wherein the reaction mixture further comprises a non-polar organic solvent, and the concentration of the non-α-tocopherol source in said solvent is in the range from about 10 g/l to about 500 g/l.

15. The process of claim 14 wherein said solvent is a $C_{5-10}$-alkane or mixture of $C_{5-10}$-alkanes, a cyclic $C_{5-10}$-alkane, or an aromatic hydrocarbon, and the concentration of the non-α-tocopherol source in said solvent is in the range from about 100 g/l to about 500 g/l.

16. The process of claim 15 wherein the trivalent metal oxide phase comprises aluminium oxide, iron(III) oxide, vanadium oxide, chromium oxide or gallium oxide.

17. The process of claim 16 wherein the trivalent metal oxide phase comprises aluminium oxide and a trivalent metal oxide selected from the group consisting of iron(III) oxide, vanadium oxide, chromium oxide or gallium oxide.

18. The process of claim 17 wherein the trivalent metal oxide phase comprises aluminium oxide and iron(III) oxide.

19. The process of claim 18 wherein the atomic ratio of the total divalent metals to the total trivalent metals is in the range from about 2:1 to about 10:1, and the atomic ratio of copper to non-copper divalent metals is in a range from about 5:95 to about 60:40.

20. The process of claim 19 wherein the atomic ratio of the total divalent metals to the total trivalent metals is in the range from about 3:1 to about 4:1.

21. The process of claim 20 wherein the divalent metal oxide phase consists essentially of copper oxide and magnesium oxide, and the trivalent metal oxide phase consists essentially of aluminium oxide and iron(III) oxide.

22. The process of claim 21 wherein the atomic ratio of copper to magnesium is in a range from about 25:75 to about 50:50, and the atomic ratio of aluminium to iron(III) is in a range from about 2:1 to about 1:2.

23. The process of claim 22 wherein the pressure is in a range from about 70 bar to about 90 bar, and the temperature is in a range from about 280° C. to about 320° C.

24. The process of claim 23 wherein the pressure is in a range from about 80 bar to about 85 bar.

* * * * *